United States Patent [19]

Gross

[11] 4,150,105

[45] Apr. 17, 1979

[54] 3-KETOSTEROID ANTIGENIC CONJUGATES, THEIR PREPARATION, ANTIBODIES AND USE

[75] Inventor: Stanley J. Gross, Encino, Calif.

[73] Assignee: Biological Developments, Inc., Encino, Calif.

[21] Appl. No.: 794,901

[22] Filed: May 9, 1977

Related U.S. Application Data

[60] Continuation-in-part of Ser. No. 528,044, Nov. 29, 1974, Pat. No. 4,022,878, which is a division of Ser. No. 253,632, May 15, 1972, abandoned, which is a continuation-in-part of Ser. No. 89,929, Nov. 16, 1970, abandoned, which is a continuation-in-part of Ser. No. 45,558, Jun. 11, 1970, abandoned, and Ser. No. 462,517, Apr. 19, 1974 which is a continuation of Ser. No. 89,929, Nov.16, 1970, abandoned.

[51] Int. Cl.$^2$ ............................................. G01N 33/16
[52] U.S. Cl. .................................... 424/1; 260/112 R; 424/12
[58] Field of Search ................ 260/112 R; 424/1, 1.5, 424/12

[56] References Cited

U.S. PATENT DOCUMENTS

| | | | |
|---|---|---|---|
| 3,940,475 | 2/1976 | Gross | 424/1 |
| 3,996,344 | 12/1976 | Gross | 424/1.5 |
| 4,041,076 | 8/1977 | Avenia et al. | 424/1 |

*Primary Examiner*—Benjamin R. Padgett
*Assistant Examiner*—Christine M. Nucker
*Attorney, Agent, or Firm*—McAulay, Fields, Fisher & Goldstein

[57] ABSTRACT

Antigenic 3-ketosteroid hapten-carrier conjugates are produced by activating a carbon atom in the 1,2 or 4 position of the steroid hapten and coupling to an immunogenic carrier through a linking agent. Specific antibodies are raised in animals and used in radioimmuno assays for the corresponding 3-ketosteroid hapten.

9 Claims, No Drawings

3-KETOSTEROID ANTIGENIC CONJUGATES, THEIR PREPARATION, ANTIBODIES AND USE

CROSS-REFERENCES TO RELATED APPLICATIONS

This application is a continuation-in-part of my copending application Ser. No. 528,044, filed Nov. 29, 1974, now U.S. Pat. No. 4,022,878, which was a divisional of my copending application Ser. No. 253,632, filed May 15, 1972, now abandoned, which was a continuation-in-part of copending application Ser. No. 89,929, filed Nov. 16, 1970, now abandoned, which, in turn, was a continuation-in-part of my application Ser. No. 45,558, filed June 11, 1970, now abandoned; of my copending application Ser. No. 462,517, filed Apr. 19, 1974, which was a continuation of application Ser. No. 89,929, aforereferenced. It is also related to my copending application Ser. No. 480,097, filed June 17, 1974 abandoned.

BACKGROUND OF THE INVENTION

1. Field of the Invention

This invention relates to immunochemical assaying. Immunochemicalassays are proving of immense value in medicine and biology for the assaying of liquid samples, especially for example, body fluid samples such as blood or urine because of the sensitivity and specificity of such assays. The present invention is concerned with assaying for 3-ketosteroid compounds, notably Δ4,3-ketosteroids and dihydrotestosterone. These compounds are mostly hormones, many of which are highly important to the proper functioning of the human body and include the sex hormones progesterone and testosterone as well as the well-known corticosteroid hormones aldosterone and cortisone. Accurate assay of these substances is of the utmost value in the diagnosis and treatment of many organic disorders.

In immunoassaying procedures, for a given target compound, a synthetic antigen is generally first prepared. Heretofore, this has usually been accomplished by coupling the target compound, through a coupling group to a carrier which confers antigenicity to the entire compound. The compound coupled to the carrier is usually known as a hapten and, when coupled, it functions as an antigenic determinant so that the antibodies produced will bind with the hapten. Thus, the antibodies produced should have a distinct and unique character, such that they will bind with only a specific compound or class of compounds. The objective in devising the synthetic hapten-carrier conjugate is to provide a compound which will generate antibodies that are specific to the target compound.

Antibodies are prepared by injecting the synthetic hapten-carrier conjugate into immunologically competent vertebrate animals, for example mammals, and recovering blood serum from them after they have had time to generate antibodies. Typical mammals are rabbits and goats.

The principal problem is usually that of producing sufficiently specific antibodies. Biological fluids such as blood and urine frequently contain very closely related compounds and it is common for antibodies to be unable to distinguish the target compound from close relatives, or sometimes even from distant ones. The antibody is then considered to be a poor one and is said to have low specificity and high cross-reactivity.

The assay itself is commonly a competitive binding assay. In a useful embodiment of such an assay, the target compound, which is not necessarily extracted, is allowed to compete with known quantities of a labeled standard to bind with a known quantity of specific antibody. From measurement of the proportion of the labeling in the standard-antibody complex that results, the amount of target compound present can be calculated. Radioactive isotope labeling is particularly convenient. Fluorescence perturbation and electron spin resonance have been used in the art. Normally it is necessary to remove any unreacted labeled standard, before making the determination on the antibody complex, although thereoretically, the determination could be made on the removed unreacted portion of the standard.

2. The Prior Art

Some thirty years ago, synthetic antigens were prepared by chemically coupling haptens to protein carriers. The antigens were administered to animals with a view to producing antibodies that would bind with the haptens. The objective was mostly to show binding. More recently the objective has been specificity of the antibody which is the quality of binding selectively with the desired compound and not with others.

Over the years there has been much research into different coupling methods and many synthetic antigens of this type have been proposed, described and prepared.

Coupling can proceed via the intermediary of a linking compound or compounds. At least two reactions are usually involved in one of which the hapten and linking compound are chemically coupled together and in the other of which the carrier and linking compound are coupled. There may be additional steps involving, for example, the coupling together of two linking compounds. It is usually desirable to couple a substantial plurality of haptens to a single carrier molecule. There are, however, known reaction sequences in which the hapten is coupled directly to the carrier in a single step, for example, by carbodiimide condensation of an amino group on one with a carboxyl group on the other to form a peptide or amide bond.

BRIEF DESCRIPTION OF THE INVENTION

Broadly stated, the present invention provides an antigen useful in raising antibodies specific to a 3-ketosteriod which antigen comprises a 3-ketosteroid hapten covalently bonded to an immunogenicity-conferring carrier, wherein, in the antigen molecule, all the functional groups of the hapten are free to exert their antigenic determinancy. Preferably, the carrier is itself immunogenic, and a substantial plurality, e.g. from 5 to 75, of hapten moieties are coupled to a single carrier moiety.

Generally, in synthesizing the antigen, a linking agent is used. The linking agent can have two functional groups, a first to couple with the 3-ketosteroid, and a second to couple with the carrier. Direct reaction of a suitable linking agent in a manner that will have the steroid functional groups free on the antigen is usually not readily feasible. Accordingly a preliminary steroid-activating reaction is advantageous. This may comprise derivatizing a suitable functional group into the steroid backbone. Alternatively, such a substance may be used as a starting material, e.g. the ring-substituted aldehyde.

According to the present invention, a particular 3-ketosteroid target compound (ultimately to be assayed) is selected as a hapten to form an antigen which is then used to form an antibody for use in the immunochemical assay of that steroid compound. These haptens have the formula:

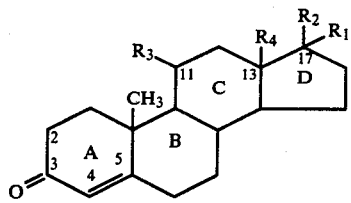

$R_1$ is selected from the class consisting of —H, —OH, —COCH$_3$, and —COCH$_2$OH; $R_2$ and $R_3$ are each selected from the class consisting of —H and —OH; $R_4$ is selected from the class consisting of —CH$_3$ and —CHO with $R_1$ being —COCH$_2$OH, $R_2$ being —H and $R_3$ being —OH when $R_4$ is —CHO; and the 4–5 bond is selected from the class consisting of the double bond shown and a single bond, $R_1$ being —OH, $R_2$ and $R_3$ being —H and $R_4$ being —CH$_3$ when the 4–5 bond is a single bond. The last-defined compound is dihydrotestosterone.

Reference hereinafter to a 3-ketosteroid indicates one of the above-defined compounds.

It may be observed that this group of 3-ketosteroids are all Δ-4,3-ketosteroids with the exception of dihydrotestosterone which can be considered as testosterone with the 4–5 double bond hydrogenated. Target compounds of particular interest are progesterone which has the formula:

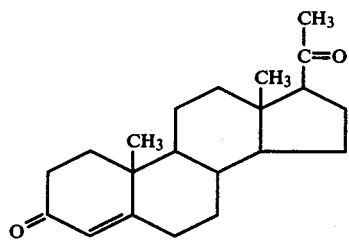

in which $R_1$ is —COCH$_3$, $R_2$ and $R_3$ are —H and $R_4$ is —CH$_3$; 17α-hydroxyprogesterone, testosterone, which has the formula;

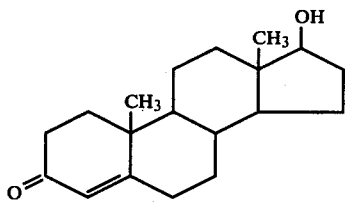

in which $R_1$ is —OH, $R_2$ and $R_3$ are —H and $R_4$ is —CH$_3$; cortisone which has the formula:

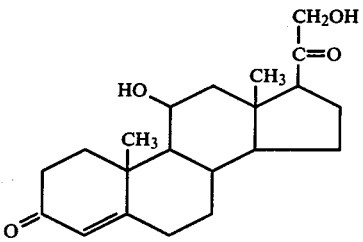

in which $R_1$ is —CH$_2$OH, $R_2$ is —H, $R_3$ is —OH and $R_4$ is —CH$_3$; hydrocortisone, being cortisone with a 17-αhydroxy substituent; and aldosterone which has the formula:

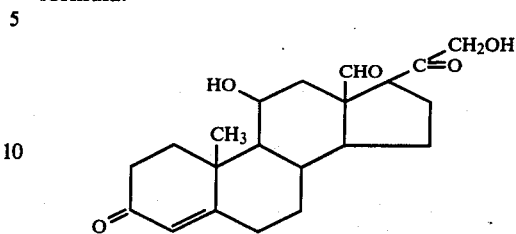

in which $R_1$ is —CO CH$_2$OH; $R_2$ is —H, $R_3$ is —OH and $R_4$ is —CHO.

The defined alternative with $R_4$ being —CHO is aldosterone which normally exists as a tautomeric equilibrium between the above-indicated structure and

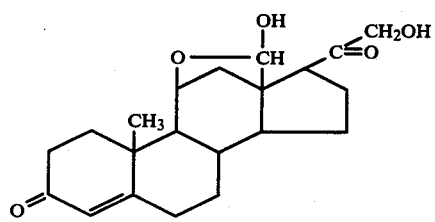

for convenience it will be considered in its aldehyde-containing form.

It is an object of the present invention to provide an antigen, and a method of producing it, which is capable of provoking the generation of antibodies specific to a 3-ketosteroid. Further objects lie in providing the antibodies, in assays using them, and in providing processes for preparing the antigens.

A feature of the invention comprises the selection, individually, of the 1, 2 or 4 carbon as the coupling site of the 3-ketosteroid. In one embodiment, a hydrocarbon moiety is favored as the first linking group to which the 3-ketosteroid ring carbon is bonded.

One method of the present invention comprises preparing a synthetic antigen which is a 3-ketosteroid hapten coupled to a carrier, the method comprising the steps of derivatizing an aldehyde-originating carbon atom into the 3-ketosteroid at the 1, 2 or 4 position and coupling the derivatized steroid to the carrier through the introduced carbon, the carrier being a macromolecule capable of conferring antigenicity.

Another method of the present invention comprises preparing a synthetic antigen which is a 3-ketosteroid hapten coupled to a carrier the method including the step of diazotizing a primary amine having a carrier couplable reactive group into the 3-ketosteroid to form an azo steroid, and coupling to the carrier through the primary amine's reactive group. The carrier is a macromolecule which confers antigenicity. For the diazotized primary amine to couple into the ketosteroid in the 1, 2 or 4 position, it is necessary for the A ring to be activated. This can be achieved by reaction of a pyrrolidine with the keto oxygen. The pyrrolidine group can be removed after diazotization by acid hydrolysis liberating 1-, 2-, or 4-azo-3-ketosteroid. Coupling through the 2 position may be preferable for the desired specificity of the antibody.

Reaction sequences according to the invention generally are selective and give good yields. In particular, cross-reactions and isomer formation are not likely so that isolation of the antigen from antigenically distinct materials is not unduly difficult as the probability of other antigenic materials being formed is low.

The present invention further comprises antigens of the formula:

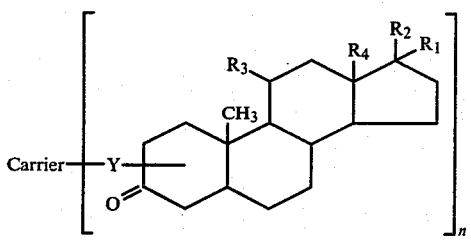

where $R_1$, $R_2$, $R_3$, and $R_4$ are as defined above, —Y— is coupled thereto at the 1, 2 or 4 position and Y is a linking moiety which includes the residue of the reaction of a first linking agent reactive group with the activated steroid and is attached to the carrier by a connective group which is the residue of a second linking agent reactive group with a reactive coupling group on the carrier, the carrier is a macromolecule conferring antigenicity, and n is an integer not exceeding the number of available reactive coupling groups on the carrier.

Thus, the antigen of this invention is the product of coupling a linking agent with the carrier and with a derivative of the steroid which derivative is activated for coupling to its 1, 2 or 4 position, and Y represents the resultant linkage connecting the carrier to the 1, 2 or 4 position of the steroid.

As indicated above, the steroid can be activated by derivatizing the reactive group into it, for instance, into one of the unsubstituted atoms of the A ring notably the 2 or 4 position.

In a preferred embodiment Y includes a phenyl ring and a two atom bridge between the phenyl ring and the steroid. The two atoms can be organic or inorganic polyvalent atoms, for example, carbon, nitrogen or sulfur. Preferably there is a double bond between the two atoms or between one of them and the steroid group. The other side of the phenyl ring can be connected either directly or indirectly to the second functional group of the linking agent which is coupled to the carrier.

In order to be capable of conferring antigenicity, the carrier will normally be antigenic itself, although it may be an incomplete antigen, becoming complete only when coupled to the hapten. To be antigenic, the carrier must be an immunogenic substance, that term being used to refer to a substance capable of eliciting production of antibodies in a host animal to which the immunogenic substance is administered. While, in general, it is believed that the terms "carrier" and "immunogenic substances" are clearly understood in the art, and the discussion herein is not meant to modify the ordinary significance of the terms, further definition is provided here for a clearer understanding of the development.

The animal to which the antigenic substance is administered must be one having an effective immunological system. The immunogenic substances must be "foreign" to the animal, in the sense of not being "self". That is, the immunogenic substance administered must not be one which is a natural body substance of the animal and would, therefore, be accordingly tolerated by the animal's immunological system.

Generally, the antibodies elicited upon injection of the immunogenic substance into the animal will be generated by the host animal and will be capable of reacting or binding with th antigen in an observable and selective way. Thus, the antibodies will display some degree of discrimination between the administered immunogenic substance and other immunogenic materials.

The requirements for immunogenicity are not fully understood. However, it appears that for a molecule to be antigenic, it must have a certain complexity and a certain minimal molecular weight. Formerly, it was thought that the lower molecular weight limit to confer antigenicity was about 5,000. However, antigenicity has recently been demonstrated with molecules having molecular weights as low as 2,000. Molecular weights of 3,000 and more appear to be more realistic as a lower limit for immunogenicity, and approximately 6,000 or more is preferred.

Exemplary immunogenic carrier materials are those set forth in Cremer et al, "Methods in Immunology," (1963), W. A. Benjamin Inc., New York, pages 65 to 113. That disclosure is herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyaminoacid. An example of an apparently incomplete antigen is the polypeptide, glucagon.

A preferred class of natural carrier materials is the proteins. Proteins can be expected to have a molecular weight in excess of 5,000, commonly in the range of from 34,000 to 5,000,000. Specific examples of such natural proteins are bovine serum albumin (BSA), keyhole limpet hemocyanin (KLH), human immunogammaglobulin (HGG), and thyroglobulin.

Exemplary of a synthetic carrier is the polyaminoacid, polylysine. Where the synthetic antigen comprises a partially antigenic carrier conjugated with a hapten, it will generally be desirable for the conjugate to have a molecular weight in excess of 6,000, although somewhat lower molecular weights may be useful.

Preferably, the natural carrier has some solubility in water or aqueous alcohol. Also preferably, the synthetic antigen is water soluble. Desirably, the carriers are nontoxic to the animals to be used for generating antibodies.

The carrier must have a, or preferably a plurality of, functional moieties by means of which it can be coupled. Of course, these groups can be introduced synthetically. Preferably, in practicing the present invention, a single carrier moiety should have a plurality of hapten moieties coupled to it, for example, from about 10 to about 70. In general, the maximum possible number of haptenic moieties per carrier molecule is preferred. Subject to steric hindrance, the maximum number will be determined by the number of reactive coupling groups on the carrier. For example, with BSA, it appears that the maximum number of haptenic moieties that can be coupled is between 60 and 70.

In preparing the antigens of the invention it is, as a practical matter, very desirable to obtain them with a high degree of purity. High antigen purity appears to be an important requisite for optimum antibody production. Accordingly, it is desirable for the process to provide for isolation of the antigen from antigenically distinct materials. The latter will normally be undesired large molecules that may confuse the immune response of animals used for producing antibodies and are very difficult to separate from the desired antigen, even chromatographically. A feature of the process of the invention is that it is designed to minimize the formation of such undesired antigenically distinct materials.

However, as a general objective, it is desirable to ensure that the derivatized steroid compound is substantially purified for the carrier-coupling step, and is especially purified of substances that could covalently couple to the carrier under the intended conditions. Purification can, for example, be effected by chromatography or fractional crystallization, preferably to a degree of 98%.

Removal of small molecule reactants and reaction products is generally desirable from the synthesized antigen. However, some small molecule substances may be useful, for example for pH control. Thus a convenient end-product form in which to recover the antigen is, in a buffered aqueous solution which is suitable for direct administration to animals.

The process of the invention can accordingly include a number of purification steps using well-known techniques such as column chromatography, dialysis and recrystallization. Further it will be generally desirable to use high purity reactants. For a natural protein carrier commercially available high purity fractions are desirable.

Antibodies can be raised by administration of an antigen of the invention to vertebrate animals, especially mammals such as goats or rabbits, using known immunization procedures. Usually a buffered solution of the antigen accompanied by Freund's adjuvant is injected sub-cutaneously at multiple sites. A number of such administrations at intervals of days or weeks is usually necessary. A number of animals, for example from three to twenty, is so treated with the expectation that only a small proportion will produce good antibodies. However, one goat producing high quality antibodies in high titer can provide sufficient for thousands of assays. The antibodies are recovered from the animals after some weeks or months.

If desired, the recovered antibodies can be purified. This can be done by absorbing the antibody on an insoluble matrix to which the target or the precursor antigen is secured so that the desired antibody binds with the target or antigen and is retained. The antibody can be recovered by elution, for example with acetic acid.

However, if the best techniques are employed throughout, it is possible that antibody purification may not be necessary.

Antibodies so produced are useful in assays for the presence of their respective targets in a liquid sample, particularly a body fluid sample, notably blood or urine.

The assay, according to the present invention, is an immunochemical method of assaying for the presence of a target according to the present invention, that target being contained in a sample. The method employs an antibody obtained by the immunologic response of a vertebrate animal to administration of an antigen according to the present invention, and the antibody is specific to the target. Further, the assay employs a standard, the standard and target competitively binding with the antibody to form an antibody-standard complex and an antibody-target complex. The antibody-standard complex has an artificially introduced radiation label so that the complex can be assayed quantitatively by measurement of the radiation emanating from it. In order for the method to be properly employed, the affinities of the antibody for the standard and for the target must be known quantitatively. In employing the method, a known quantity of the sample and a known quantity of the standard are allowed to compete for binding with a known quantity of the antibody. The radiation emanating from the antibody-standard complex so formed is determined so that the quantity of antibody-bound standard can be calculated and the quantity of target in the sample can be deduced. This deduction is carried out by attributing any difference between the quantity of bound standard determined and the quantity expected, based on the known binding characteristics of the antibody, to binding of the antibody with the target.

In an embodiment of the assaying procedure, the introduced label is radioactive and the antibody-standard is separated from any non-complexed, labeled material after allowing competition binding and before determination of the radiation emanated.

In another embodiment of the assaying method, the introduced label is fluorescent and the standard is provided with a chemical moiety giving it a fluorescence spectrum overlapping the natural fluorescence spectrum of the antibody. The complex can then be assayed by measurement of the perturbation of the antibody fluorescence due to binding with the standard.

The standard is a substance known to bind with the antibody and can be, for example, the target, the antigen used to raise the antibody, or the hapten used to make the antigen. Similarly, it can be a similar antigen having the same hapten bound to a different carrier, but at the same position on the hapten. Conveniently, where the radiation constitutes radioactive emission, such as beta or gamma rays, the standard can carry the radioactive label in the form of a radioactive isotope, e.g., tritium, $I^{125}$, or $C^{14}$, although, as an alternative, the antibody can be labeled.

When separation of the complex from the unreacted standard is necessary, as is normally the case with radioactive labeling, this can be effected by phase separation, insolubilizing of one of the components to be separated, etc. Thus, with a labeled antibody, the use of an antigenic standard having a plurality of antibody binding sites causes the antibody-standard complex to precipitate while, if the target is a small molecule, the antibody-target complex will remain in solution. Alternatively, the antibody can be insolubilized, as described elsewhere in the specification, and the standard labeled, so that unreacted standard stays in solution and can easily be separated from the complex.

One example of such a separation is the addition of saturated ammonium sulfate to the complexed mixture. The mixture, with the added ammonium sulfate, is then centrifuged which results in deposition of most of the protein, including the antibody-standard complex. The antibody-standard complex can then be removed as a solid and measurement carried out on this solid. Alternatively, the uncomplexed liquid standard is subjected to measurement of radiation emanation.

A further possibility is to absorb the standard with dextran-charcoal, after allowing for competition binding, and to then make the scintillation count for radiation on the liquid phase containing the antibody-standard complex following separation of the solid phase which contains the unreacted standard. In this case, the standard is labeled and is a small molecule, especially a radioactive isotope labeled target molecule.

While the count for radiation is normally made upon the antibody-standard complex, as this is either more convenient or is believed to reduce experimental error, it will be clear that where there is a separation of unbound, labeled material from the antibody-standard complex, the determination of the radiation emanating from the antibody-standard complex can equally well be made by measuring the radiation emanating from the unreacted, labeled material. From this measurement, the difference from the known amount of labeled material added can be calculated.

The term "radiation" is used in an ordinary dictionary sense and refers to energetic emissions originating from individual atoms or molecules which are generally attributed to internal changes within the atom or molecule. These emissions are in contrast to physical phenomena, such as, for example, precipitations which are the result of the inter-molecular or inter-atomic effects, and may require a large-scale cooperation of a great number of atoms or molecules to be meaningfully expressed. Radiation is significant for immunoassays as it provides a means of remotely monitoring the behavior of very small quantities of matter.

Thus, in addition to energetic emissions, radiation includes such phenomena as fluorescence and electron spin resonance. Fluorescence usually requires excitation by exposure to ultraviolet light, but the product is radiation. Thus, energy, usually in the form of light, is emitted as a result of intra-molecular change.

Where fluorescence is the form of radiation measured, it is feasible for the assay to be conducted without any separation of materials. Thus, antibodies, which are naturally fluorescent, have an absorption spectrum and an emission spectrum. If the standard chosen is a molecule having, as a label, a chemical group which fluoresces in spectra overlapping the antibody, then, when the standard complexes with the antibody, the natural fluorescence of the antibody is perturbed by that of the standard, and this perturbation can be measured. When the emission spectrum of the standard overlaps the absorption spectrum of the antibody, fluorescence enhancement will be observed from the complex at the antibody emission wavelength, and when the absorption spectrum of the standard overlaps the emission spectrum of the antibody, fluorescence quenching will be observed from the complex at the antibody emission wavelength. Comparable effects can be displayed using polarization perturbation.

Electron spin resonance labeled assays can also be conducted without the need for separation. A paramagnetic labeling group, such as a nitroxide ring, is attached, for example, to the standard. When subjected to a microwave frequency magnetic field, an electron spin resonance spectrometer can detect distinct resonance peaks characteristic of the nitroxide ring label. When the standard combines with antibody, these peaks are substantially extinguished, providing a direct indication of the degree of binding.

DESCRIPTION OF THE PREFERRED EMBODIMENTS

Four principal routes are contemplated as illustrative of the preferred practice of the process of the invention, and these will be described as Reaction Sequences, A, B, C and D respectively. Reaction Sequence A may be described as amino bridging, B as thiomethylating, C as enamine derivatizing and D as ethylene bridging.

In reaction Sequence A, the 3-ketosteroid is formylated to give the 2-aldehyde derivative as an intermediate and this is reacted with a primary aromatic amine to form an imine bridge from the phenyl group of the aromatic amine to the 3-ketosteroid. The phenyl group is then coupled to a carrier and for this purpose will normally carry a suitable functional group remote from the amine. An example of such a functional group is a carboxyl which is convenient for amide coupling to the lysine residues of a proteinic carrier.

Formylation will normally be carried out under alkaline conditions in which case any peripheral carbonyl group the 3-ketosteroid has will need protecting to reduce the risk of polymerization or modification of the steroid D ring.

In Reaction Sequence B the 3-ketosteroid is reacted with a thiol and formaldehyde to derivatize a thiomethylene group into the 4-position. Desirably the thiol carries a convenient group for coupling to the carrier. For coupling to a proteinic carrier an amino group is convenient although it requires to be blocked, for example with an acetyl group, against activity in the derivitization step. After deblocking the amino group can be diazotized into a tyrosyl or histidyl ring on the protein assuming it contains one.

This procedure is not contemplated for dihydrotestosterone owing to the inactivity of its 4-carbon, but is generally useful for Δ-4,3-ketosteroids.

In Reaction Sequence C a saturated heterocyclic secondary amine is reacted with the 3-ketosteroid to produce an enamine compound in which the keto oxygen is displaced and a double bond is introduced into the A or B ring of the steroid. This activates the A ring so that an appropriate linking group can be coupled at the two or four position. A particularly convenient mode of coupling is by diazotizing a derivatized primary aromatic amine, for example, para aminobenzoic acid. The diazotized compound can then be coupled to a carrier, for example, a protein by reaction with the derivative. In the particular case of para aminobenzoic acid this derivative is a carboxyl group which can be coupled to a protein by carbodiimide condensation with an available lysine residue. After diazotization and before carrier coupling the secondary amine group must be removed from the three position and the keto group reformed. This can be done by simple acid hydrolysis.

As in Reaction Sequence A protection of any carbonyl group that the 3-ketosteroid carries on the D ring is desirable during any alkaline conditions, for example, during the diazonium coupling step.

Reaction Sequence D again commences with the 2-aldehyde 3-ketosteroid or prepares it in a preliminary step. An ethylene bridge is then formed by reaction with a alkylidenephosphorane in the manner of the Wittig reaction. Again, the alkylidenephosphorane will carry a convenient functional group for coupling to the carrier, for example, a carboxyl group.

These Reaction Sequences will now be described in more detail.

Reaction Sequence A

This may be depicted graphically as follows:

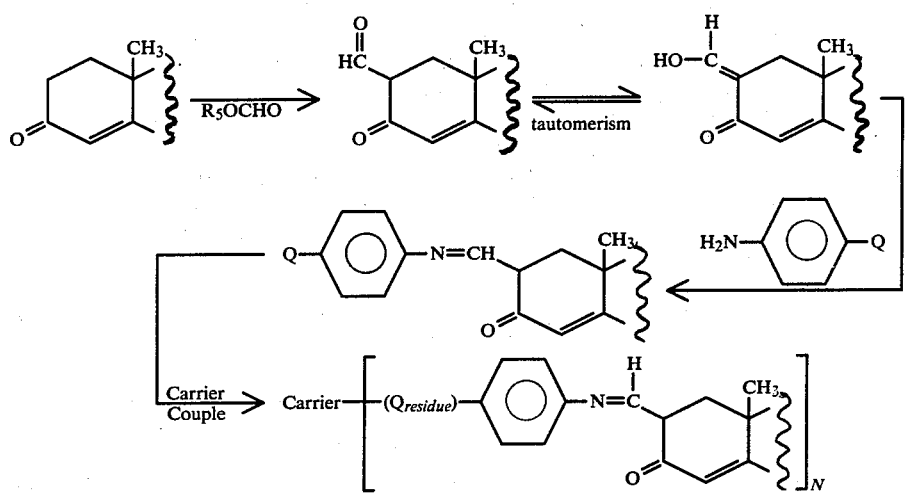

where $R_5$ is an alkyl group having from 1 to 6 carbon atoms and Q includes a reactive moiety that may be coupled to a further reactive group on the carrier, its residue being essentially non-reactive in this sequence, and is bonded to its accompanying aryl at any position with one or more bonds provided that the amino group is available for reaction. For example, Q may include one or more further phenyl rings conjugated to the first, but it is contemplated that not more than four such rings would be useful and, further, that not more than 20 carbon atoms in an aliphatic chain would be useful. The reactive moiety on Q may conveniently be a carboxyl group. Alternatively, Q may require further reaction to provide a suitable coupling group, for example, it may be nitro, being reduced to amino for coupling, the reactive moiety being the reactive moiety.

Formylation

The reagents and conditions for this step are largely conventional formylation ones. The formylating reactant is an alkyl formate having from 1 to 6 carbon atoms in its alkyl moiety. Ethylformate is convenient. This is reacted with the 3-ketosteroid in the presence of a strong base.

It is important to avoid the presence of hydroxyl groups (other than steroid hydroxyls) in this reaction. Accordingly the solvent is anhydrous and non-hydroxylic; for example anhydrous benzene or tetrahydrofuran. Equally, the base although a strong one, is not an alkali metal hydroxide. Another alkali metal nonhydroxylic base, for example sodium or potassium hydride or amide is used.

The 3-ketosteroid, the formylating agent and the base are dissolved in the solvent at concentrations of from about 0.1% to the limits of their solubilities with around 10% by weight preferred, if feasible. The relative proportions of the reactants should be within about 10 or 20 percent of stoichiometric, with a slight excess of the formylating agent and base being preferred for efficient utilization of the 3-ketosteroid.

These are reacted together for from 6 to 72 hours depending upon the reaction temperature which can be from room (20° C.) to the boiling point of the solvent. Refluxing for 24 hours is convenient.

This yields the water-soluble metal salt. For the next step of the reaction it is desirable to obtain the solid 2-formyl-3-ketosteroid which is normally described as its tautomer, 2-hydroxymethylene-3-ketosteroid. This is done via solvent extraction from an acidified aqueous solution of the sodium salt. The latter can be obtained by one of two routes. The solid reaction product can be collected by filtering off the reaction medium, washed with ether, and dissolved in aqueous acid, liberating the substituted steroid. Alternatively the reactants can be removed by extraction with ether and the aqueous fraction acidified to liberate the substituted steroid. By either route, the liberated product is then extracted with benzene and crystallized.

Imine-Bridging

This reaction is comparable with a conventional condensation of an aldehyde and an amine to form an imine, the 2-hydroxymethylene grouping behaving as the aldehyde. Accordingly conditions known to be effective for the conventional condensation reaction are broadly applicable to this step of the present invention.

The 2-hydroxymethylene-3-ketosteroid from the formylation step is reacted in an organic solvent, for example benzene, with a slight excess of up to about 10 percent above stoichiometric of a primary aromatic amine for example p-amino benzoic acid, in the presence of a trace of p-toluene sulfonic acid catalyst. The reaction mixture is refluxed for from 12 to 72 hours, 24 being normally appropriate. The 2-[4'-carboxyphenylimino (3-ketosteroid)] product is separated. In some cases, for example with dihydrotestosterone the product may crystallize out.

The iminoketosteroid product is then coupled to a carrier through the available carboxyl group. This is conveniently effected by using a protein or synthetic polypeptide carrier and coupling to the amino group of a lysine residue by carbodiimide condensation to form an amide or peptide bond. Isobutylchloroformate and thionylhalides are alternatives to a carbodiimide.

The carrier is dissolved in water or aqueous methanol or ethanol, depending upon its solubility as known in the art. The concentration is not critical, depending at the lower end of the possible range upon practical operating convenience and at the upper upon the solubility of the carrier. A likely range is from about 1 to about 50 weight percent of carrier to solution, with around 10 weight percent being convenient. The solution is acidified with HCl to a pH of not less than about 3, preferably from 3.9 to 4.1.

The iminoketosteroid product is dissolved in water or alcohol. Since its solubility is moderate, an excess can be used in suspension. The excess is taken up as the dissolved iminoketosteroid product reacts; however, too great an excess is not desired so that a practical limit is about 15 weight percent iminoketosteroid product to solvent. Convenience dictates a lower limit of about 0.5 weight percent iminoketosteroid product and a preferred range of from 1 to 10 weight percent.

These two solutions, one of which may be a suspension, are mixed and carbodiimide is added as a solid. Preferably, there is a slight stoichiometric excess of carbodiimide over iminoketosteroid product to maximize material usage.

The reaction mixture is then stirred for from 6 to 8 hours. The stirring can be continued longer, but 8 hours is normally sufficient for the reaction to go to completion. Some reaction should occur after about 1 hour.

In this step the temperature range is desirably from 4° to 25° C. although temperatures from −10° C. to 60° C. can normally be used.

The coupled product is purified and the desired antigenic conjugate isolated by column separation, for example on a Sephadex gel filtration column with a phosphate buffer to pH 7.4–7.6. As indicated above, if the 3-ketosteroid is one whose R substituents include a keto group, for example, aldosterone, cortisone or a progesterone, this will probably need to be protected in the formylation reaction because the strongly alkaline conditions of that reaction render the substituent keto group reactive.

Suitable means of protection are known to the art or can be devised. For example, Gardi et al, *Journal of Organic Chemistry* vol. 28 p. 1440 (1963), describes blocking aldosterone with a diethyl acetal of an aldehyde or ketone, e.g. of acetone, and Fried and Edwards "*Organic Reactions in Steroid Chemistry*" vol. 1 pp. 410–411 (van Nostrand Reinhold New York) describes blocking cortisone with a bismethylene dioxy compound.

These blocking groups are removed by acid hydrolysis which can conveniently be effected prior to imine-bridging.

Reaction Sequence B

This may be depicted graphically as follows:

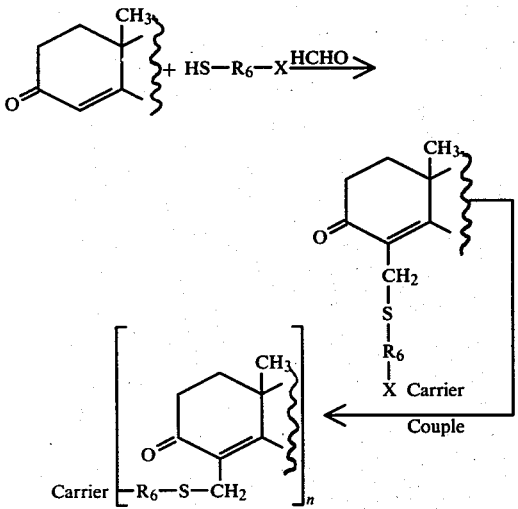

where $R_6$ and X are as described below and the carrier is coupled to $R_6$ through a connective group being the residue of the reaction of X with a reactive group on the carrier.

Thio methylene Derivatization

In this step the 3-ketosteroid is heated with formaldehyde (or paraformaldehyde) and a thiol in a basic organic solvent, refluxed for from 6 to 48 hours e.g. 24, and cooled.

The concentration of the reactants in the solvent is preferably up to about 10 percent, by weight and the formaldehyde and thiol are preferably in slight stoichiometric excess over the 3-ketosteroid for example up to about 10 or 20 percent excess.

The thiol can have the following structure:

$$HS-R_6-X$$

wherein $R_6$ is selected from the class consisting of aromatic moieties with from 6 to 14 carbon atoms, especially, for example, phenyl and of aliphatic groups with from 1 to 4 carbon atoms, and X is a reactive group that can be coupled to the carrier. For a proteinic carrier X can conveniently be amino or carboxylic. X will normally be spatially somewhat removed from the HS-group and where $R_5$ is phenyl, should be in the 3 or 4 position.

$R_6$ can be aliphatic, for instance N-propyl, for testosterone but is preferably aromatic for progesterone. p-amino thiophenol is specifically contemplated.

When X is amino it should be protected from reactivity in this step by blocking, for example with an acetyl group.

Suitable bases are, for example, triethylamine and triethanolamine. Water is added to the cooled reaction mixture and the solid product collected by filtration. The water insoluble product is purified by column chromatography to yield in the case where the thiol is acetyl-blocked p-aminothiophenol, the 4 (N-acetyl-p-amino phenylthiomethylene)-3-ketosteroid.

If the product is blocked, it is then unblocked by acid hydrolysis e.g. by reflux with 1 to 2 N ethanolic HCL, the product being precipitated with water.

Many reaction sequences are available for coupling the thiomethylene steroid to the carrier by reaction between X and a functional group on the carrier. A number of such reactions are described in U.S. patent application Ser. No. 253,632, filed May 15, 1972. A convenient route where —X is —$NH_2$ and the carrier is a protein having available phenols or other diazotizable rings is by diazotization in two stages. The conditions for this reaction are conventional. It proceeds in two stages. First the amino group is converted to the diazonium salt by reaction with nitrous acid and then this salt is coupled to the protein under alkaline conditions.

Two aqueous solutions are prepared at 0°–5° C. One is a solution of the aminothiomethylenesteroid acidified with HCl to a pH of from 0.5 to 2.0, preferably from 1.0 to 1.5. The concentration is dictated by convenience and solubility, being from about 0.1 to 10 percent by weight, of the aminoderivative with approximately 4 percent being preferred. The other solution is a simple, aqueous solution of sodium nitrite which, for example, can be a 1 percent solution.

At a temperature of from 0° to 5° C., the sodium nitrite solution is added, dropwise, to the iminoketosteroid solution, to an end point with potassium iodide-starch paper. Excess nitrous acid is decomposed with sulfamic acid. Under the acid conditions, the diazonium compound forms the salt.

The carrier protein is dissolved at about 0.1 weight percent in an aqueous medium at pH adjusted to be from 9 to 11 with sodium hydroxide. The diazonium salt solution from the previous step is added dropwise to this protein solution at a temperature maintained at from 0° to 5° C., maintaining also the pH at from 9 to 11 with sodium hydroxide. The mixture is stirred to completion of the reaction which takes from about 20 minutes to 1 hour. During this reaction, the mixture develops a pink-toned color indicating diazo coupling.

The resulting solution of the synthesized antigen is purified and isolated from other antigenic materials by dialysis, preferably against a phosphate buffer.

For more effective purification a preliminary dialysis against a stronger base can be made, provided that the 3-ketosteroid is base-stable. 17-α-hydroxyprogesterone is not so stable.

If desired the solid antigen can be obtained by lyophilization, but the aqueous solution remaining after thorough dialysis is normally suitable for administration to animals.

Reaction Sequence C

The reaction with a Δ-4,3-ketosteroid may be depicted as follows:

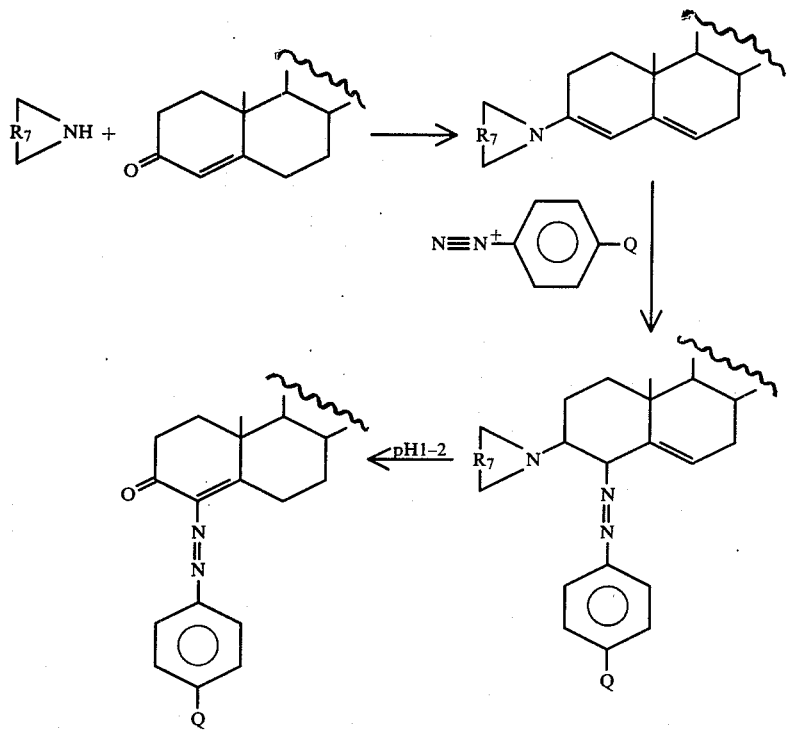

In the case of a 3-ketosteroid which has no unsaturation the reaction proceeds somewhat differently and may be depicted as follows:

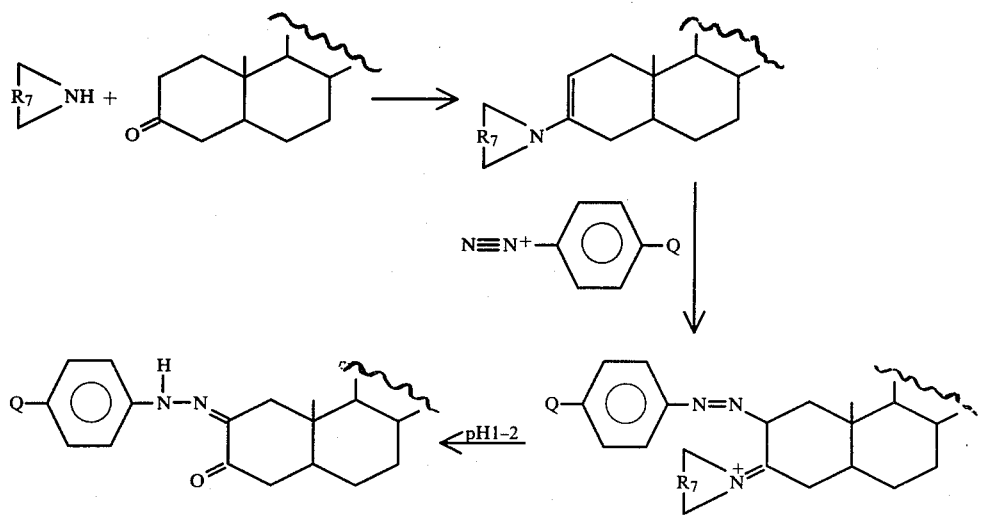

In the foregoing sequences, Q is as in Reaction Sequence A and a preferred embodiment of Q is a carboxyl group. $R_7$ is a moiety which completes the ring to form the saturated heterocyclic secondary amine. $R_7$ preferably comprises from four to eight ring atoms which may or may not be substituted. Preferred ring atoms are carbon, nitrogen and oxygen. Particularly preferred for the secondary amine are pyrrolidine and piperidine. In these cases $R_7$ comprises four and five methylene groups, respectively.

It will be seen that the cyclic secondary amine displaces the keto oxygen atom and at the same time, introduces a double bond into the steroid. Where the A ring of the steroid already contains a 3-4 double bond then the double bond introduced in this reaction appears in the B ring in the 6-7 position. In this case it is the 4 position which is activated for diazotization. Where the steroid is saturated, the double bond is introduced at the 2-3 position and it is the 2 position which is activiated for diazotization.

The azo-group shown at the end of the first formula sequence shown above can isomerize with its tautomer hydrazone group shown at the end of the second formula sequence shown above. As shown, in the first sequence the azo form predominates and in the second the hydrazone form predominates.

The reaction with the cyclic secondary amine is carried out in an organic solvent. The solvent must be miscible with the cyclic secondary amine and must, of course, also be a solvent for the steroid. Hydroxyl ions are to be avoided since the enamine is base-unstable and may be degraded. Accordingly, several organic solvents are suitable including the polar solvents, tetrahydrofuran (THF), dioxan, and primary alcohols. The preferred solvent is methanol. The reaction is preferably acid catalyzed and for this purpose a trace of an organic acid such as paratoluene sulfonic acid can be used. The reaction goes at room temperature or the mixture may be heated to reflux. At room temperature, one or two hours may be necessary whereas at reflux less time will be sufficient.

As indicated above, the proportions of reactants are preferably close to molar equivalents although a slight excess of the cyclic secondary amine may be desirable to insure that all the steriod is used. In most cases, the product will crystallize out. Pyrrolidine progesterone has reasonably pure, yellow crystals which can, if necessary, be re-crystallized from alcohol for improved purity.

The enamine compound with its reactive 2 or 4 carbon can be derivatized in a number of ways to introduce a group capable of being coupled to a suitable carrier. For example, reaction with the ester of a haloacetic acid followed by acid hydrolysis will, while still so removing the cyclic secondary amine, form a carboxy alkyl derivative. The carboxyl can then be readily coupled to a proteinic carrier by carbodiimide condensation. However, a preferred route is the one that is shown, namely diazotization. The azo group has been shown to be a particularly advantageous group for hapten coupling and it is possible that it may function as a better linking group than some other linking group in the sense of leading to the production of more specific antibodies.

The diazotization reaction is a standard reaction and the conditions and reagents known by the art to be effective for diazotization can be employed. However, some exemplary conditions will be described. In this reaction a primary aromatic amine is diazotized into the enamine ketosteroid. For purposes of description reference will be made to p-benzoic acid (PABA) it being understood that other compounds can also be used.

Two aqueous solutions are prepared at 0° to 5° C. One is a solution of PABA acidified with HCL to a pH from 0.5 to 2.0, preferably from 1.0 to 1.5. The concentration is dictated by convenience, the solubility being from about 0.1 to 10% weight PABA with approximately 4% being preferred. The other solution is a simple, aqueous solution of sodium nitrite which, for example can be a 1% solution.

At a temperature of from 0.5° to 8° C. the sodium nitrite solution is added drop-wise to the PABA solution to an end point with potassium iodide starch paper. Excess nitrous acid is decomposed with sulfamic acid. Under the acidic conditions the diazonium compound forms a salt.

The enamine keto steroid is dissolved at about 0.1% by weight in an aqueous alcoholic solvent system, for example one having a high proportion of methanol. The pH of this solution is adjusted to the range of from 9 to 11 with sodium hydroxide. The diazonium solution from the previous step is added drop-wise to this enamine ketosteroid solution at a temperature maintained at from 0° to 5° C. the pH being adjusted and maintained at from 9 to 11 with sodium hydroxide. The mixture is stirred to completion of the reaction which takes from about 20 minutes to 1 hour.

The cyclic secondary amine group is removed and the keto group reformed by acidifying the mixture to a pH of about 1 to 2 with dilute hydrochloric acid (e.g., one-tenth normal). The azo or hydrazone steroid is then purified by chromatography for instance, on a silica gel column.

As mentioned above, it may be necessary to protect keto groups that are present on D ring substituents and this can be done in the manner described above for Reaction Sequence A, for example with diethylacetylacetone.

Reaction Sequence D

This reaction may be depicted as follow:

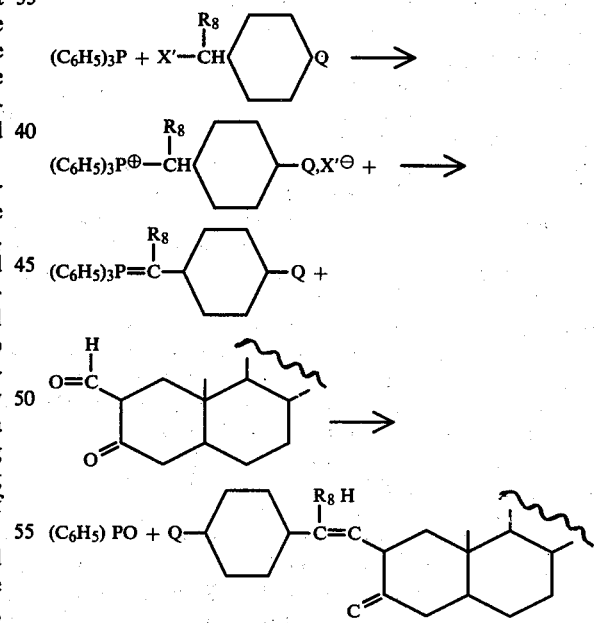

In this sequence $R_8$ is hydrogen or lower alkyl having not more than 6 carbon atoms and $X'$ is a halogen; Q is as before. The aklylidine phosphorane is synthesized by reacting triphenylphosphine with an appropriately derivatized methylene halide. This reaction proceeds in a non-hydroxylic, organic solvent, for example, benzene, toluene or tetrahydrofuran and can be completed by refluxing for from fifteen minutes to one hour or will proceed at room temperature requiring from one to twelve hours. The product is the corresponding triphenylphosphonium salt. This is separated and purified by re-crystallization.

The alkylidene phosphorane is liberated by reaction with a base under anhydrous conditions. Suitable bases are, for example, the alkali metal hydrides, sodium hydrides or lithium hydrides. A suitable solvent is, as before, an organic solvent, such as benzene. This reaction proceeds reasonably quickly and the 2-aldehyde, 3-ketosteroid obtained, for example, from the first step of Reaction Sequence A, is then added to the reaction mixture. The characteristic Wittig reaction then proceeds either at room temperature in one to twelve hours or by refluxing for from fifteen minutes to one hour and produces the desired end product, the omega-substituted 2-ethylene 3-ketosteroid.

While the preferred phosphorane is the triphenyl, other phosphoranes known to react in the Wittig reaction may be used. For example, the phenyl groups may be replaced by alkyl substituted groups or alkoxy groups or alkyl groups, or mixtures of the foregoing, in each case the alkyl groups having not more than eight carbon atoms. The end product is then purified by column chromatography.

One desirable group for Q is a nitro group as this does not take part in the foregoing reaction sequences. A carboxyl group would potentially be more desirable inasmuch as it can then couple directly to a protein. However, a carboxyl requires protection through the foregoing reaction sequence, for instance, by esterifying it. It must then be liberated from the end product.

Where Q is a nitro group after purification of the 3-ethylene 3-ketosteroid, Q is reduced to an amino group. This may be effected in a suitable solvent system using a palladium/carbon catalyst by bubbling hydrogen through under pressure. The catalyst is filtered off, the solvent evaporated and the amino product recovered by re-crystallization. The product can be fractionally crystallized to purify it.

The 2-ethylene, 3-ketosteroid can then be coupled to a carrier, for example, a protein through the Q group. Where Q is carboxyl, this can be effected by carbodiimide condensation with an amino group on, for example, a protein carrier in the manner described above. Where Q is converted to an amino group this can readily be coupled to any carrier containing diazotizable aromatic rings by diazotizing the amino group and coupling to such rings. Most natural proteins contain tyrosine residues and histidine residues whose rings are diazotizable and accordingly are suitable for this coupling. Diazotizing conditions are similar to those described elsewhere herein. Essentially a solution of the 2-ethylene, 3-ketosteroid derivative is acidified to a pH of from 0.5 to 2.0 and while maintaining a temperature in the range of from 0° to 5° C., a solution of sodium nitrite is added to an end point with potassium iodide/starch paper. Excess nitrous acid is decomposed with sulfamic acid. The resulting diazonium salt is then coupled to the carrier by adding its solution drop-wise to a solution of the carrier whose pH has been adjusted to be in the range of from 9 to 11. The temperature is still maintained at from 0° to 5° C. and the pH is continuously adjusted with sodium hydroxide to keep it in the range of from 9 to 11. The mixture is stirred to completion of the reaction which takes from about twenty minutes to one hour.

The resulting antigenic conjugate is then purified and used as described for the other antigens that are the subject of this invention.

In a further sequence an antigen is formed with an azo bridge to the 2-position of the hapten.

This can be achieved by coupling an aromatic diazonium compound with the 2-hydroxymethyl steroid described above. The reaction conditions are as described above, and the aromatic diazonium compound will carry a functional group, e.g. carboxyl, capable of being coupled to the carrier. After diazo coupling, the hydroxymethyl, or formyl group remains in situ and is accordingly removed in a separate step prior to carrier coupling.

A somewhat modified antigen of interest, especially for testosterone is one in which the A ring of the steroid hapten contains a second double bond in addition to the 4-5 double bond (e.g. 1-2) though the resulting antibody is intended primarily for assaying for the corresponding steroid having only the one, 4-5, double bond in the A ring. The object of this is to provide an antibody well able to recognize the double bond and distinguish the corresponding saturated compounds for example to bind well with testosterone and have a low cross-reactivity with dihydrotestosterone.

Such an antibody is expected to bind well with the hapten having two double bonds. However, these appear to occur rarely, if at all, in body fluid samples. In their absence from the sample an assay will not be prejudiced by the antibody's ability to bind with them.

In order that those skilled in the art may be better enabled to practice the invention, the following examples are given. These should be considered as exemplary only, and as not limiting in any way the full scope of the invention as covered in the appended claims.

EXAMPLE 1

Reaction Sequence A-Coupling of Dihydrotestosterone
(a) Preparation of 2-hydroxymethylene-dihydrotestosterone One gram of dihydrotestosterone was dissolved in 8 mls. of anhydrous benzene and to it was added 300 mg. sodium hydride, followed by 0.4 ml. ethyl formate. This was stirred for 12 hours under nitrogen. The sodium salt of the 2 hydroxymethylene derivative was filtered, washed with benzene, then with hexane, and dried. Precipitation in ice cold dilute (0.1 N) hydrochloric acid gives crude 2 hydroxymethylene dihydrotestosterone. This is recrystallized from ether-petroleum ether.

(b) Preparation of 2-(p-carboxyphenylamine) dihydrotestosterone

The following materials were measured out:
2 hydroxymethylene dihydrotestesterone—100 mg.
p-aminobenzoic acid (PABA)—84 mg.
Dry Benzene—25 ml.
p-toluene sulfonic acid—1.2 mg.

The solution of the hydroxymethylenedihydro testosterone, PABA and p-toluene sulfonic acid in benzene is allowed to reflux for 12 hours using a Dean Stark trap. The precipitated imine derivative is filtered and washed with benzene.

(c) Coupling to proteinic carrier, bovine serum albumin (BSA)

The following materials were weighed out:
BSA—500 mg.
Dihydrotestosterone imine—60 mg.
Soluble carbodiimide—25 mg.

The BSA is dissolved in 20 ml. of water. To it is added a solution of the dihydrotestosterone derivative in very dilute base (0.001–0.01 N NaOH). The pH of the solution is adjusted to 6–7. 75 mg of the carbodiimide is added and the solution is stirred for 6–8 hours at 4° C. It is then lyophilized and the residue dissolved in 5 ml. pH 7.6 phosphate buffer. This is passed down a G-25 Sephadex column using a phosphate buffer at pH 7.6 as eluent. The protein faction is collected and lyophilized.

EXAMPLE 2

Coupling of Testosterone to BSA 2-hydroxymethylene testosterone is synthesized by the method described in JACS 76, 552 (1954). The carboxyphenylimine derivative is then formed and coupled to BSA by the methods described in Example 1, with similar results.

EXAMPLE 3

The procedure of Example 1 is repeated except that equivalent amounts respectively of cortisone and hydrocortisone are used in place of dihydrotestosterone, and the keto group of the steroid is protected during formylation. Similar results are obtained. The protection is effected by reaction of the steroid with diethylacetalacetone and is removed after formylation by dilute HCL.

EXAMPLE 4

Reaction Sequence B—Coupling 17-α-hydroxyprogesterone (a) Preliminary Preparation of the N-Acetyl-blocked

| | Derivative of P-Aminothiophenol | |
|---|---|---|
| 2.0 g | (0.013 mole) | p-aminothiophenol |
| 1.5 cc. | (0.016 mole) | acetic anhydride |
| 1.9 g. | (0.023 mole) | sodium acetate in 6 cc. H$_2$O |
| 1.3 g. | (0.035 mole) | HCL (1.08 cc. conc. HCl in 30cc H$_2$O) |

The aminothiophenol is dissolved in the aqueous HCL solution and the acetic anhydride added. The aqueous sodium acetate is then added, and the mixture stirred in an ice water bath for 10 minutes. The resulting solid is filtered, washed with water and recrystallized from aqueous methanol. This N-acetyl derivative, p-mercaptoacetanilide, is used in the next step.

(b) Preparation of the 4-organothiomethylene derivative of 17-α-hydroxyprogesterone 265 mg. of 17-α-hydroxyprogesterone and 300 mg. p-mercaptoacetanilide is dissolved (by warming) in 3cc. triethanolamine. Three hundred and sixty-five mg. (about 0.365cc.) of 38% aqueous formaldehyde is added and the resulting mixture heated at 110°–115° C. for 5-6 hours. The reaction mixture is cooled to room temperature and 10cc. of water added. The resulting solid is filtered, washed with water and dried. The yield of crude solid was 550 mg. with a Rf value of 0.22.

(c) Purification of the acetyl-blocked 4 (p-aminophenyl-thiomethylene)-17-α-hydroxyprogesterone 350 mg. of the crude material is chromatographed on a 120 g. silica gel column using CHCl$_3$: MeOH (97:3) as the solvent system. Those fractions containing the desired material are combined and the solvent removed under reduced pressure. The yield was 95 mg.

(d) Hydrolysis of the N-acetyl derivative

The acetyl derivative above is taken up in 30 cc. ethanol, 3 cc. of conc. HCL added, and the resulting solution refluxed for one hour. The progress of the hydrolysis is checked periodically by thin layer chromatography to avoid decomposition by prolonged heating. One hundred cc. of water is then added, and the solution evaporated to a final volume of approximately 50 cc. The pH of the resulting aqueous solution is then adjusted to 7.5 with dilute sodium hydroxide and the resulting precipitate filtered and dried. The yield was 55 mg., and the precipitate gave the following test results.

| TLC (thin layer chromatograph) Chloroform:methanol | 97:3 |
|---|---|
| Rf value | 0.29 |

The nuclear magnetic resonance spectrum is consistent with the structure:

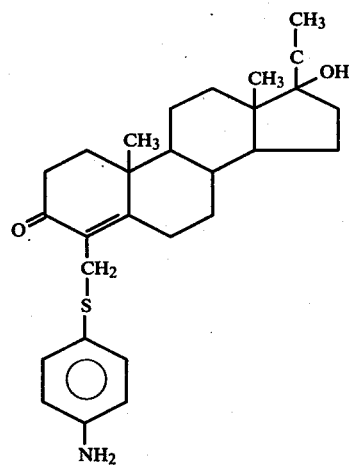

(e) Coupling of the 17-α-hydroxyprogesterone Derivative to bovine serum albumin

The following materials were weighed out:

| 4-(p-aminophenylthiomethylene) - 17 - hydroxyprogesterone | 100 mg. |
|---|---|
| Sodium Nitrite | 15 mg. |
| Bovine Serum Albumin (BSA) | 600 mg. |

The 100 mg. of the hydroxyprogesterone derivative is dissolved in 1 ml. of 1 N HCL and the solution cooled to 0°–5°. To it is added a cold (0.5°) solution of sodium nitrite (15 mg.) in 0.5 ml. water to an end point with starch iodide paper. Excess nitrous acid is decomposed with a few crystals of sulfamic acid. The cold diazonium salt solution is added dropwise to a cold (0°–5° C.) solution of 600 mg. BSA in 10 ml. water, previously adjusted to pH 9–10 with 2 N sodium hydroxide. During the addition the pH is maintained between 9 to 11 with 2 N sodium hydroxide and the temperature maintained at 0.5° C. After the addition is complete the solution is stirred at 0.5° C. for one hour at pH9. It is transferred to a dialysis tubing and dialyzed against six liters of 0.1 molar diabasic sodium phosphate at 4° C. for 6 days with daily change of the dibasic sodium phosphate solution.

It is next dialyzed for 2–4 days against 0.1 molar phosphate buffer (6 L) pH 7.4–7.6 with daily change of the buffer solution.

The optical density at 280 nm. was determined as 1.4 for a 0.1% solution.

EXAMPLE 5

Example 4 is repeated except that equivalent amounts of progesterone, aldosterone, cortisone, hydrocortisone and testosterone respectively are used in place of hydroxyprogesterone. Similar results are obtained.

EXAMPLE 6

Each of Examples 1 to 5 is repeated except that keyhole limpet hemocyanin, human immunogammaglobulin and thyroglobulin respectively are used in place of bovine serum albumin. Similar results are obtained.

EXAMPLE 7

Example of Wittig Reaction
(a) Preparation of p-nitrobenzyltriphenylphosphonium chloride A solution of 26.3 g (0.10 moles) of triphenylphosphide and 17.2 g (0.10 moles) of p-nitrobenzyl chloride in 50 ml of benzene is refluxed for 2 hours. After cooling the solid is collected and washed with benzene. Crystallization from carbon tetrachloride petroleum ether gives colorless crystals, m.p. 278°–280° C.
(b) Reaction of p-nitrophenylmethylenetriphenylphosphorane with hydroxymethylene testosterone To a stirred solution of 0.3 g (0.01 moles) of p-nitrobenzyltriphenylphosphorane chloride in dry benzene and under dry nitrogen is added 0.85 g (0.013 moles) of butyl lithium. After stirring for 2 hours testosterone is added and the reaction mixture is stirred for an additional 4 hours It is then neutralized with 1N HCL, shaken with water and the organic layer is separated. The desired product 2-(p-nitrophenylymethylene)testosterone is isolated by column chromatography.
(c) Reduction of 2-(p-nitrophenylethylene) testosterone to 2-(p-aminophenylethylene) testosterone.

A solution of the nitro compound in acetone-aqueous sodium hydroxide is treated with sodium hydrosulfite and refluxed for about 30 minutes. The product is then extracted and chromatographed on silica gel to give pure 2-(p-aminophenylethylene)-testerone.

EXAMPLE 8

Raising of Antibodies

Approximately 2 mg. doses of antigen in 0.1% aqueous solution with Freund's adjuvant are injected at multiple, subcutaneous sites in rabbits. The injections are repeated at intervals according to known immunization procedure. The rabbits are bled at intervals and the active serum is collected and used without purification.

The testosterone antigen of Example 5 was used to raise an antibody which gave the following cross-reactivities:

|  | 1st Rabbit | 2nd Rabbit |
|---|---|---|
| Testosterone | 100% | 100% |
| Dihydrotestosterone | 12% | 20% |
| 5 - α- androstan - 3 - α- 17 - β- diol | 4.5% | 1% |
| 5 - α- androstan - 17 - β - ol - 3 - one | 15.1% | 20.8% |
| 1,4 - androstediene - 17 - β- ol - 3 - one | 11.9% | 16.4% |
| 1,5 α- androstene - 17 - β ol - 3 - one | 18.0% | 7.3% |

In a variation of reaction sequence A, [A(var.)], a different reactant is used in the second step to couple to the formaldehyde group which was introduced at the 2 position of the hapten in the first step. Instead of a primary aromatic

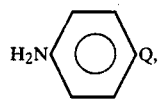

its diazotization product, the corresponding diazonium ion,

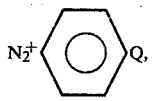

is used. The reaction is carried out under cold, alkaline conditions conventional for diazo coupling, and leads to coupling at the 2 carbon of the steroid. The previously introduced formaldehyde, or hydroxymethylene, group can be removed by cold acid hydrolysis to yield the desired 2 (Q-phenyl)hydrazone progesterone. The intermediate is the corresponding 2(Q-phenyl)hydrazone-2-hydroxymethylene steroid.

The product can be coupled to a carrier through Q in the manner described above for related products.

This sequence of synthesis is representative of the broader idea of derivatizing into the 2 or 4 position of the 3-ketosteroid *any* group that will satisfy the requirements of (1) activating the 2 or 4 carbon atom for coupling with a diazonium ion, and (2) being capable of being removed after coupling, under non-disruptive conditions. The similarity to Reaction Sequence C will be apparent.

This A(var.) sequence is believed to be novel in several respects. The fact that the hydroxymethylene group can activate the steroid's 2 carbon for diazo coupling is thought not to have been previously recognized. The activation is presumably substantially assisted by the keto group in the 3 position. It is known that diazo coupling can be effected to some saturated carbons that are subject to certain conditions of activation, (see, e.g., P.A.S. Smith "Open-chain Nitrogen Compounds," W. A. Benjamin, New York), but any teaching of the possible relevance of this to appropriately derivatized, non-aromatic steroids is not known to the inventor. The idea of diazonium coupling into the ring of a 3-ketosteroid is also thought to be novel. Finally, to be able to achieve this coupling by introducing an activating group that can be removed without disrupting the product, is novel and unobvious.

The antibodies prepared from the resulting antigen have excellent specificity, which may be helped by the hydrazone bond coupling directly to a ring atom of the hapten.

EXAMPLE 8

(a) Synthesis of 2 hydroxymethylene Progesterone 540 mg. of sodium methoxide was suspended in 20 mls. dry benzene. 740 mg. of ethylformate was aded to the stirred mixture at room temperature. This solution was added to a solution of 3.14 gm. of progesterone in 20 mls. dry benzene with stirring. The mixture was stored until a gelatinous orange precipitate separated and was then allowed to stand overnight. To it was added 75–100 mls. water and the aqueous layer separated. It was extracted with 100 mls. ether and the ether discarded. The acqueous layer was acidified with 2 NHCL (pH 1–1.5), extracted with ether, the ether extract divided, filtered and evaporated. The residual oil was chromatographed on silica gel and the first fraction coming through contained the 2-hydroxymethylene progesterone (mp. 155°-160° C.). This was recrystallized from methanol to give material having a melting point of 160°-161° C. Approximately 500 mg. of product was obtained.

(b) Progesterone-2-(p-carboxylphenyl) hydrazone 137 mg. p-aminobenzoic acid was dissolved in about 10 mls. in HCL and cooled to 0°-5° C. To it was added a cold (0°-5° C.) solution of 69 mg. sodium nitrite in 1-2 mls. water very gradually. This diazonium salt solution was allowed to stand for about 20 min. in an ice bath after which time any excess nitrous acid (determined with starch-iodide paper) was decomposed with sulfamic acid.

342 mg. hydroxymethylene progesterone was dissolved in about 20 mls. water adjusted to pH 12 with 1N NaOH. This solution was cooled to 0°-5° C. and to it was added the cold diazonium salt solution, dropwise. The pH was maintained between 11-12 with 1N NaOH and the temmperature maintained at 0°-5° C. Once the addition was complete the reaction mixture was stored at 0°-4° C. for 2 hours. It was then acidified to pH 1-1.5 with conc. HCL and extracted with ethyl acetate. The ethyl acetate solution was separated, dried with sodium sulfate and concentrated. Addition of ether precipitated the derived progesterone-hydrazone.

(c) Coupling of Progesterone Hydrazone to BSA 250 mg. BSA was dissolved in about 10 mls. H₂O. To it was added a solution of 50 mg. progesterone hydrazone in 5 mls. H₂O made alkaline with 1 N NaOH. The pH of the solution was adjusted to 6-6.5. 75. mg. carbodiimide was added and the solution stirred overnight in the cold room (=5° C.). It was dialyzed against 6 L of 0.5% sodium bicarbonate solution for 4 days with daily changes of the bicarbonate solution. It was next dialyzed against 6 L of 0-1 M (pH 7.6) phosphate buffer for 2 days with daily changes of the buffer. The O.D. was then read to determine concentration and the solution adjusted with distilled water to 1% protein concentration.

OD 1.4=0.1% protein.

(d) The following cross reactivities of the progesterone antisera with related steroids were obtained:

| Material | % Cross reactivity |
|---|---|
| Progesterone | 100 |
| 17 α-hydroxy progesterone | 0.3 |
| 11 α- hydroxy progesterone | 0.3 |
| 6 β- hydroxy progesterone | 0.2 |
| hydrocortisone | >0.1 |

The antigen was used to raise antibodies which were recovered and used for assaying, all in accordance with the methods described above. Tritiated progesterone was used as the marker.

Radioimmune Assay

The radioimmune assay is performed by incubating various dilutions of antisera obtained from animal bleedings, with $^3$H-3-ketosteroid (New England Nuclear) in the presence of buffer at 4° C. After two hours a neutral, saturated ammonium sulfate solution is added. The resultant precipitates are sedimented by centrifugation at 3,000 rpm for 15 minutes at 4° C. and the supernates are decanted off. Aliquots of 0.5 l. of the supernates are added to counting vials, together with 0.5 ml. water and 10 ml. Aquasol and counted for tritium. The addition of increasing amounts of unlabelled 3-ketosteroid to a fixed amount of $^3$H-3-ketosteroid and antiserum results in a competitive inhibition of the $^3$H-3-ketosteroid bound to antibody.

This enables a standard curve for the antibody to be established showing the variation of inhibition of binding with concentration.

The specificity of the antibody is then determined by allowing for competitive binding of the known concentrations of the antibody with known concentration of the labelled standard and successive potential cross-reactants. The cross-reactivity is defined according to the method of Abrahams as the relative quantity of target to cross-reactant that produces 50% inhibition, multiplied by 100 for percentage.

As a practical matter, only cross-reactants that could conceivably be present in the sample are significant. Cross-reactivity with other substances may be irrelevant, if they are not expected to be present in the sample, e.g., serum or urine.

Thus calibrated, the antibody can be used in assays, for example by the method of the fourth preceding paragraph, the sample under assay constituting the source of unlabelled 3-ketosteroid.

If desired, the antibodies of this invention can be insolubilized, or otherwise supported, on a solid matrix. Examples of materials to which the antibody can be attached are glass, synthetic polymers, synthetic resins, and cellulose. The material to which the antibody is attached or otherwise insolibilized can have an extensive, continuous form, such as a sheet, or it can be in the form of discrete particles of desired size. The antibody can be secured to the material in a number of ways.

Among the methods for attaching or otherwise insolubilizing the antibody to a solid matrix are covalent bonding, van der Waal's forces, hydrogen bonding, etc. Thus, the methods for attaching the antibody to the solid matrix are relatively weak intermolecular forces, covalent bonds, or the adsorptive forces attributable to a porous surface. An example of van der Waal's forces occurs with the adhesion of an antibody to a predominantly hydrophobic plastic surface, such as a polyolefin. Apparently, there is hydrophobic bonding to the hydrophobic amino acid residues of the antibody.

Some of the methods for bonding of the antibody to a solid matrix are discussed in Weliky and Weetall, *Immunochemistry*, Vol. 2, pages 293-322 (1965).

Another method for conveniently covalently bonding the antibody to a solid is by diazotizing available amino groups on the antibody into available, activated, aromatic rings on the solid material.

It may be desirable to modify the material, particularly for the purpose of securing the antibody to it. Thus, for covalent bonding, carbodiimide condensation, with the formation of an amide bond between the antibody and the material, can be used. For this purpose, the material should have available primary, non-aromatic amine groups or carboxyl groups to couple with, respectively, available carboxyl or amino groups on the antibody. An amino glass suitable for this purpose is known. Suitable synthetic resins or polymers may be available, in addition, or existing resins can be modified. Similarly, many derivatized celluloses are known, and cellulose can, in general, be provided with appropriate groups.

In attaching the antibody to the substrate material, it is normally desirable to ensure that the active binding site of the antibody remains available and accessible. This can be facilitated by blocking the site before coupling to the support material, and unblocking thereafter. Blocking can be conveniently effected by complexing the antibody with the hapten for which it is specific and deblocking can be effected with an eluting agent, for example, acetic acid or urea.

For sorption on a porous surface, another method for insolubilizing the antibody on a solid matrix, it is desirable for the pore size of the material, e.g., porous particles, to be selected for optimum accommodation of the antibody.

What is claimed is:

1. A synthetic antigen having the following formula:

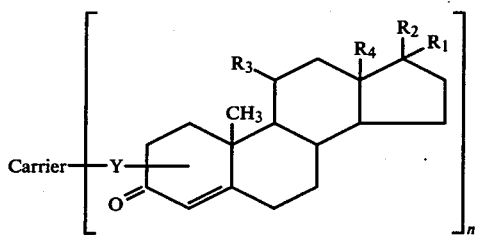

where $R_1$ is selected from the class consisting of —H, —OH, —COCH$_3$ and —COCH$_2$OH; $R_2$ and $R_3$ are each selected from the class consisting of —H and —OH; $R_4$ is selected from the class consisting of —CH$_3$ and —CHO with $R_1$ being —COCH$_2$OH, $R_2$ being —H, and $R_3$ being —OH when $R_4$ is —CHO; where the 4–5 bond is selected from the class consisting of the double bond shown and a single bond, $R_1$ being —OH, $R_2$ and $R_3$ being —H and $R_4$ being —CH$_3$ when the 4–5 bond is a single bond; wherein the antigen is the product of coupling a linking agent with the carrier and with a derivative of the steroid which derivative is activated for coupling to its 1,2 or 4 position, and Y represents the resultant linkage connecting the carrier to the 1,2 or 4 position of the steroid; the carrier is a macromolecule conferring antigenicity; and n is an integer not exceeding the number of available reactive coupling groups on the carrier.

2. The synthetic antigen of claim 1 wherein n is 5 to 75.

3. The synthetic antigen of claim 2 wherein the steroid moiety is selected from the class consisting of aldosterone, cortisone, hydrocortisone, progesterone, 17-α-hydroxyprogesterone, testosterone and dihydrotestosterone.

4. The synthetic antigen of claim 2 wherein the carrier is a protein selected from the class consisting of bovine serum albumin, keyhole limpet hemocyanin, human immunogammaglobulin, thyroglobulin and poly-1-lysine.

5. Antibody raised by, directed to and binding with the antigen of claim 2.

6. The antibody of claim 5 insolubilized by securing it to a solid matrix.

7. An immunochemical method of assaying for the presence of a 3-ketosteroid hapten target as defined in claim 1, wherein said method employs an antibody obtained by the immunologic response of a vertebrate animal to administration of an antigen according to claim 1 and wherein said antibody is specific to the target, said method also employing a standard, the antibody binding with the target to form an antibody-target complex and competitively binding with the standard to form an antibody-standard complex, the antibody-standard complex having an artificially introduced radiation label enabling the complex to be assayed quantitatively by measurement of radiation emanating from it, the affinities of the antibody for the standard and for the target being known quantitatively, said method comprising allowing a known quantity of the sample and a known quantity of the standard to compete for binding with a known quantity of the antibody and determining the radiation emanating from the antibody-standard complex, thereby enabling the quantity of antibody-bound standard to be calculated and the quantity of target in the sample to be deduced.

8. The method of claim 7 where the label is radioactive and the antibody-standard complex is separated from any non-complexed labelled material after allowing competition binding and before determination of the emanated radiation.

9. The method of claim 7 wherein the label is fluorescent and the standard is provided with a chemical moiety giving it a fluorescence spectrum overlapping the natural fluorescence spectrum of the antibody, whereby the complex can be assayed by measurement of the perturbation of the antibody fluorescence due to its binding with the standard.

* * * * *